(12) United States Patent
Hwang et al.

(10) Patent No.: US 11,801,496 B2
(45) Date of Patent: Oct. 31, 2023

(54) CATALYST FOR PREPARING 1,2-PENTANEDIOL AND METHOD FOR PREPARING 1,2-PENTANEDIOL BY USING SAME

(71) Applicant: KOREA RESEARCH INSTITUTE OF CHEMICAL TECHNOLOGY, Daejeon (KR)

(72) Inventors: Young Kyu Hwang, Daejeon (KR); Do Young Hong, Daejeon (KR); Jaesung Kwak, Daejeon (KR); Pandharinath Pravin Upare, Daejeon (KR); Dong Won Hwang, Daejeon (KR); Jung Ho Lee, Daejeon (KR); Jong-San Chang, Daejeon (KR); Joung-mo Cho, Daejeon (KR); U Hwang Lee, Daejeon (KR); Kyung Ho Cho, Daejeon (KR); Su Kyung Lee, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 17/270,252

(22) PCT Filed: Jul. 4, 2019

(86) PCT No.: PCT/KR2019/008195
§ 371 (c)(1),
(2) Date: Feb. 22, 2021

(87) PCT Pub. No.: WO2020/009493
PCT Pub. Date: Jan. 9, 2020

(65) Prior Publication Data
US 2021/0346873 A1 Nov. 11, 2021

(30) Foreign Application Priority Data

Jul. 6, 2018 (KR) .................. 10-2018-0078842
Jan. 28, 2019 (KR) .................. 10-2019-0010591

(51) Int. Cl.
*B01J 23/835* (2006.01)
*B01J 23/62* (2006.01)
*C07C 29/141* (2006.01)

(52) U.S. Cl.
CPC ........... *B01J 23/835* (2013.01); *B01J 23/622* (2013.01); *C07C 29/141* (2013.01)

(58) Field of Classification Search
None
See application file for complete search history.

(56) References Cited

U.S. PATENT DOCUMENTS

2014/0243562 A1   8/2014 Omeis et al.

FOREIGN PATENT DOCUMENTS

JP    2014523864 A    9/2014
JP    2015514810 A    5/2015
(Continued)

OTHER PUBLICATIONS

Machine translation of Shigetaka et al., JP 2015107954 A (Year: 2015).*

(Continued)

*Primary Examiner* — Coris Fung
*Assistant Examiner* — Keling Zhang
(74) *Attorney, Agent, or Firm* — STIP Law Group, LLC (57) ABSTRACT

The present disclosure relates to a catalyst for preparing 1,2-pentanediol from furfural and/or furfuryl alcohol, and more particularly to a catalyst, which is configured such that a catalytically active metal containing both at least one transition metal and tin (Sn) is supported on a basic support (Continued)

and is capable of increasing reaction selectivity for 1,2-pentanediol, and a method of preparing 1,2-pentanediol using the same.

7 Claims, 2 Drawing Sheets

(56) References Cited

FOREIGN PATENT DOCUMENTS

| JP | 2015107954 A | 6/2015 |
|---|---|---|
| KR | 20140011387 A | 1/2014 |

OTHER PUBLICATIONS

Dutta et al., Advances in conversion of hemicellulosic biomass to furfural and upgrading to biofuels, Catal. Sci. Technol., 2012, 2, 2025-2036 (Year: 2012).*
International Search Report of PCT/KR2019/008195, dated Oct. 17, 2019, English translation.
Gotz, D et al, Aqueous Phase Hydrogenolysis of Bio-Derivable Furfuryl Alcohol to Pentanediols Using Copper Catalysts, Catalysts, 2017, vol. 7, p. 50 (inner pp. 1-7), Catalyst, New York, USA.
Linus Pauling, The Crystal Structure of Magnesium Stannide, The Journal of the American Chemical Society, Dec. 1923, vol. 45, No. 12pp. 2777-2780, American Chemical Society, Washington DC, USA.
Homer Adkins AND Ralph Connor, The Catalytic Hydrogenation of Organic Compounds Over Copper Chromite, A Communication from the Laboratory of Organic Chemistry of the University of Wisconsin, Mar. 6, 1931, vol. 53, pp. 1091-1095, American Chemical Society, Washington DC, USA.
The extended European search report of EP19 83 0795, dated Mar. 22, 2022.
Pravin P. Upare et al, An integrated process for the production of 2,5-dimethylfuran from fructose, Green Chemistry, May 5, 2015, vol. 17, pp. 3310-3313, The Royal Society of Chemistry, London, United Kingdom.
Jong-Min Lee et al, Direct Hydrogenation of Biomass-Derived Butyric Acid to n-Butanol over a Ruthenium-Tin Bimetallic Catalyst, ChemSusChem Communications, 2014, vol. 7, pp. 2998-3001, Wiley-VCH Verlag GmbH & Co. KGaA, Weinheim, Germany.
Jong-Min Lee et al, Direct Hydrogenation of Biomass-Derived Butyric Acid to n-Butanol over a Ruthenium-Tin Bimetallic Catalyst, ChemSusChem, 2014, vol. 7, pp. 2998-3001, Wiley-VCH Verlag GmbH & Co. KGaA, Weinheim, Germany.

* cited by examiner

CATALYST FOR PREPARING 1,2-PENTANEDIOL AND METHOD FOR PREPARING 1,2-PENTANEDIOL BY USING SAME

CROSS-REFERENCE TO RELATED APPLICATIONS

This application is the U.S. National Phase under 35 U.S.C. § 371 of International Application No. PCT/KR2019/008195 filed on Jul. 4, 2019, which in turn claims the benefit of Korean Application Nos. 10-2018-0078842 filed on Jul. 6, 2018, and 10-2019-0010591 filed on Jan. 28, 2019, the disclosures of which are incorporated by reference into the present application.

TECHNICAL FIELD

The present disclosure relates to a catalyst for a hydrogenation reaction for preparing 1,2-pentanediol from furfural and/or furfuryl alcohol, and to a method of preparing 1,2-pentanediol using the same.

BACKGROUND ART 1,2-pentanediol is a colorless or pale yellow liquid, has two hydroxyl groups (—OH) and an alkyl group having five carbon atoms, and is characterized in that it is miscible both with water and with oil-type solutions. Due to these properties, 1,2-pentanediol is used as a moisturizer, which is an active ingredient that prevents skin from becoming dry due to environmental conditions and weather in the cosmetic field, and is used for baby products, bath products, makeup products, cleansing products, skin care products, and hair care products.

Moreover, 1,2-pentanediol has antibacterial activity, so when used together with other preservatives, it is capable of playing a role of increasing the antibacterial activity, and thus may be used as an alternative to existing preservatives.

In general, 1,2-pentanediol is prepared from n-pent-1-ene, obtained from petrochemicals, using peroxides. Here, the diester of 1,2-pentanediol formed as an intermediate has to be removed, which generates a large amount of wastewater. In addition, since n-pent-1-ene has a very low boiling point, it is difficult to handle, so it is desirable to find a simple synthesis route that is feasible on an industrial scale.

As an alternative thereto, it is possible to synthesize 1,2-pentanediol using furfural or furfuryl alcohol, which is a material capable of being obtained from renewable materials, as a reactant, and since furfural or the like may be obtained in large amounts from grain waste containing sugar, research thereto is ongoing in view of the use of waste and environmental protection.

Figure 1:
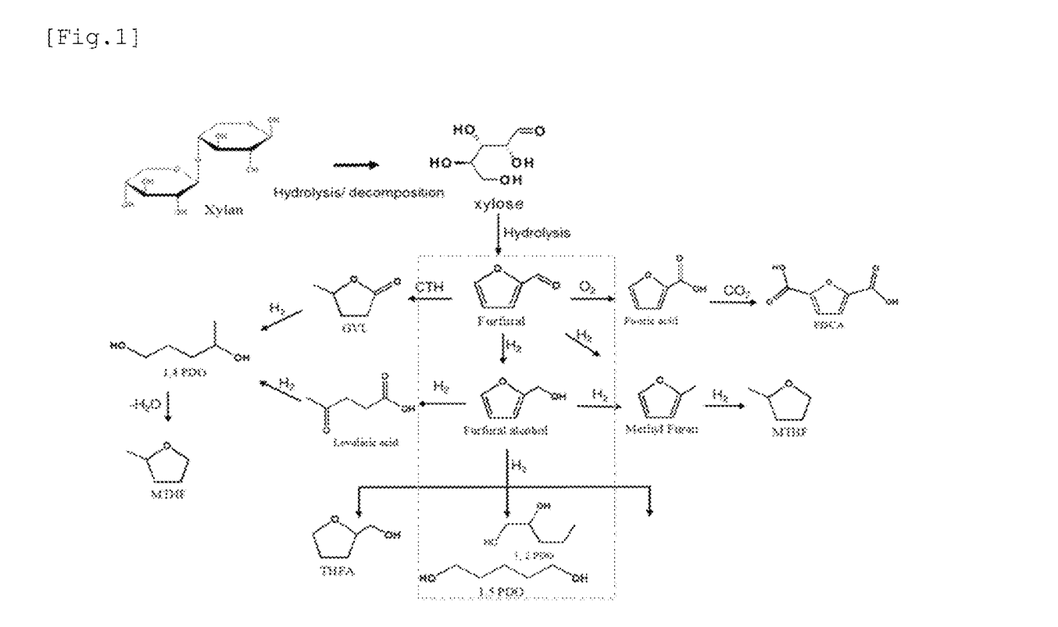
FIG. 1 shows a reaction scheme in which 1,2-pentanediol and other compounds synthesizable from furfural or furfuryl alcohol derived from xylan are produced.

As shown in FIG. 1, in literature it has been reported that various compounds are formed through the hydrogenation or hydrogenolysis of furfural or furfuryl alcohol.

In Non-Patent Document 1 [Journal of American Chemical Society 45, 3029 (1923)], it has been reported that a mixture of furfuryl alcohol, 1-pentanol, tetrahydrofurfuryl alcohol, 1,2-pentanediol and 1,5-pentanediol is obtained through hydrogenolysis/hydrogenation of furfural in the presence of platinum black at room temperature.

Additionally, in Non-Patent Document 2 [Journal of American Chemical Society 53, 1091 (1931)], it has been reported that 40% of 1,2-pentanediol and 30% of 1,5-pentanediol are obtained by reacting liquid furfuryl alcohol with hydrogen at 175° C. using copper chromite as a catalyst.

Research is ongoing into methods capable of increasing the reaction yield of 1,2-pentanediol, the use of which has increased in cosmetics, among mixtures generated through the hydrogenation reaction of furfural or furfuryl alcohol. Japanese Patent Application Publication No. 2015-107954 (Jun. 11, 2015) discloses a method of preparing 1,2-pentanediol from furfuryl alcohol using an alkaline compound composed of an alkali metal or alkaline earth metal compound in the presence of a copper-containing metal catalyst, but the reaction yield of 1,2-pentanediol thus prepared is reported to be less than 50% (Patent Document 1).

In addition, Korean Patent Application Publication No. 10-2014-0011387 (Jan. 28, 2014) discloses a method of synthesizing 1,2-pentanediol from furfural or furfuryl alcohol using a catalyst in which at least one metal compound selected from among platinum, rhodium, ruthenium, nickel, and palladium is supported on a support, and the maximum yield of 1,2-pentanediol is reported to be 80% using, for example, a platinum oxide catalyst (Patent Document 2).

As described above, since the method of preparing 1,2-pentanediol through the hydrogenation reaction of furfural or furfuryl alcohol is regarded as an important technology capable of utilizing biomass, various catalysts therefor are being developed. Research and development on a novel catalyst having higher reaction selectivity for 1,2-pentanediol and a method of preparing 1,2-pentanediol using the same are continuously required.

The reactions described above may be carried out in a gas phase or a liquid phase, and a liquid-phase reaction is more advantageous than a gas-phase reaction in view of controlling the reaction temperature, whereas the gas-phase reaction is more advantageous in view of productivity.

The present disclosure is intended to develop a gas-phase reaction or liquid-phase reaction method capable of preparing 1,2-pentanediol from furfuryl alcohol and/or furfural in an efficient and environmentally friendly manner, and an efficient catalyst therefor.

The inventors of the present disclosure ascertained that the reaction selectivity of 1,2-pentanediol may be increased when using a catalyst system of a specific metal combination, among surveyed catalyst systems, to prepare 1,2-pentanediol at a high yield compared to existing catalyst systems, thus culminating in the present disclosure.

DISCLOSURE

Technical Problem

The present disclosure has been made keeping in mind the problems encountered in the related art, and an objective of the present disclosure is to provide a catalyst system for a gas-phase or liquid-phase reaction with high reaction selectivity for 1,2-pentanediol in the hydrogenation reaction of furfural or furfuryl alcohol, and a method of preparing 1,2-pentanediol using the same.

Technical Solution

In order to accomplish the above objective, the present disclosure provides a catalyst for use in the preparation of 1,2-pentanediol by reacting a starting material including at least one of furfural and furfuryl alcohol with hydrogen. More specifically, the present disclosure provides a catalyst for preparing 1,2-pentanediol, in which the catalyst is configured such that a catalytically active metal is supported on a basic support, and the catalytically active metal includes at least one transition metal and tin (Sn). Preferably, the transition metal is at least one selected from among transition metals of Groups 8, 9, 10, and 11, and is more preferably at least one selected from among Ru, Pt, Rh, Ir, Pd, Ni, Co, and Cu.

In an embodiment of the present disclosure, the basic support may be at least one selected from among alkali metal oxide, alkaline earth metal oxide, lanthanide oxide, zinc oxide, spinel, perovskite, hydrotalcite, calcium silicate, basic zeolite, and basic metal organic frameworks (MOFs), and examples thereof may include MgO, CaO, BaO—ZnO, MgO—$Al_2O_3$, ZnO, $ZrO_2$, $CeO_2$, hydroxyapatite, $Mg_2Al_2O_4$, $ZnAl_2O_4$, $BaTiO_3$, $ZnTiO_3$, $Cs_2O$, CsX (in which X=OH, Cl, Br, or I), Zr-based MOFs, Mg-based MOFs, Ca-based MOFs, Sr-based MOFs, Ba-based MOFs, $Mg_2Al_2O_4$, $ZnAl_2O_4$, $BaTiO_3$, $ZnTiO_3$, and the like, but are not limited thereto, so long as the support is basic.

In another embodiment of the present disclosure, the catalytically active metal may be supported in an amount of 0.1 to 90 wt % on the support.

In another embodiment of the present disclosure, the amount of tin in the catalytically active metal may vary depending on the type of transition metal that is used therewith, but may be 20 to 99.5 mol %, preferably 30 to 98 mol %, more preferably 50 to 96 mol %, and even more preferably 75 to 94 mol %, based on the total amount of the catalytically active metal.

In another embodiment of the present disclosure, the catalyst may be subjected to reduction without firing in an oxidizing atmosphere before use.

In addition, the present disclosure provides a method of preparing 1,2-pentanediol through the hydrogenation reaction of a starting material including at least one of furfural and furfuryl alcohol in the presence of the catalyst described above.

In another embodiment of the present disclosure, furfural and/or furfuryl alcohol may be compounds derived from biomass.

In another embodiment of the present disclosure, in the method of the present disclosure, furfural may be obtained through dehydration of xylose resulting from hydrolysis of xylan, and furfuryl alcohol may be obtained through hydrogenation of the furfural.

In another embodiment of the present disclosure, in the method of the present disclosure, the reaction of the starting material and hydrogen may be carried out at a temperature of 100 to 200° C. and a hydrogen pressure of 5 to 50 bar, and the reaction may proceed in a liquid phase.

In another embodiment of the present disclosure, in the method of the present disclosure, the reaction of the starting material and hydrogen may be carried out at a temperature of 200 to 300° C. and a hydrogen pressure of 5 to 100 bar, and the reaction may proceed in a gas phase.

In another embodiment of the present disclosure, in the method of the present disclosure, the starting material may be allowed to react in a liquid phase by diluting the starting material in any one solvent selected from among 1-propanol, isopropanol, 1-butanol, 2-butanol, and mixtures thereof.

In another embodiment of the present disclosure, in the method of the present disclosure, the catalyst may be subjected to reduction without firing in a liquid phase using a reducing agent at the time of reduction before use.

In another embodiment of the present disclosure, in the method of the present disclosure, the catalyst may be used in an amount of 0.001 to 25 wt % based on the amount of the starting material.

In another embodiment of the present disclosure, in the method of the present disclosure, the solvent may be used in an amount of 1 wt % to less than 100 wt % based on the amount of the starting material.

Advantageous Effects

According to the present disclosure, 1,2-pentanediol can be produced at a high yield through a gas-phase reaction or a liquid-phase reaction of hydrogen and a starting material including at least one of furfural and furfuryl alcohol using a catalyst system formed by supporting a catalytically active metal including at least one transition metal and tin (Sn) on a basic support.

BEST MODE

Unless otherwise defined, all technical and scientific terms used herein have the same meanings as those typically understood by those skilled in the art to which the present disclosure belongs. Generally, the nomenclature used herein is well known in the art and is typical.

As used herein, when any part is said to "comprise" or "include" any element, this does not mean that other elements are excluded, and such other elements may be further included unless otherwise specifically mentioned.

The catalyst used to prepare 1,2-pentanediol through the reaction of hydrogen with a starting material including at least one of furfural and furfuryl alcohol according to the present disclosure is configured such that an active metal including at least one transition metal and tin (Sn) is supported on a basic support.

The starting material including at least one of furfural and furfuryl alcohol may be subjected to a direct hydrogenation reaction in a single step to obtain a mixture of 1,2-pentandiol and 1,5-pentandiol. The reaction yield of 1,2-pentandiol may be adjusted depending on the activity of the catalyst component that is used.

The transition metal may be at least one metal selected from among transition metals of Groups 8, 9, 10, and 11, and preferably is at least one selected from among Ru, Pt, Rh, Pd, Ir, Ni, Co, and Cu, or is at least one selected from among Ru, Pt, Ni, Co, and Cu.

The amount of tin may be 20 to 99.5 mol %, preferably 30 to 98 mol %, more preferably 50 to 96 mol %, and even more preferably 75 to 94 mol %, based on the total amount of the catalytically active material.

A heterogeneous catalyst system in which the catalytically active metal is supported on the support is preferable, and the support, which is basic, may include alkali metal oxide, alkaline earth metal oxide, lanthanide oxide, zinc oxide, spinel, perovskite, hydrotalcite, calcium silicate, basic zeolite, basic metal organic frameworks (MOFs), etc. Examples of the basic support may include MgO, CaO, BaO—ZnO, MgO—$Al_2O_3$, ZnO, $ZrO_2$, $CeO_2$, hydroxyapatite, $Mg_2Al_2O_4$, $ZnAl_2O_4$, $BaTiO_3$, $ZnTiO_3$, $Cs_2O$, CsX (in which X=OH, Cl, Br, or I), Zr-based MOFs, Mg-based MOFs, Ca-based MOFs, Sr-based MOFs, Ba-based MOFs, $Mg_2Al_2O_4$, $ZnAl_2O_4$, $BaTiO_3$, $ZnTiO_3$, and the like, but are not limited thereto, so long as the support is basic.

The support is preferably at least one selected from among ZnO, MgO, $CeO_2$ and $ZrO_2$, and more preferably includes ZnO or MgO.

The catalytically active metal is preferably supported in an amount of 0.1 to 90 wt % on the support, and when the amount of the catalytically active metal falls within the above range, an optimal effect is exhibited between the catalytic activity and the supported amount.

In a method of preparing the catalyst system in which the catalytically active metal is supported on the support, a support may be formed first, and an active metal precursor may be supported through an impregnation process, or a material used as the support and a catalytically active metal precursor may be simultaneously coprecipitated, and thus the catalytically active metal may be supported.

The type of precursor of the transition metal in the active metal is not particularly limited, but at least one selected from among halogen salts, nitrates, oxalates, carbonates, sulfates, nitrosyl acetate and nitrosyl nitrate may be used.

The type of precursor of tin, which is contained in the active metal of the present disclosure, is not particularly limited, but at least one selected from among $Sn(NO_3)_2$, $SnCl_2$, $SnCl_4$, $Sn(OC(CH_3)_3)_4$, $SnCl_2.2H_2O$, $SnBr_2$, $SnI_2$, $Sn(OH)_2$, $SnSO_4$, $Sn(CH_3COO)_2$, $Sn(CH_3COCHCOCH_3)_2$, SnO, $SnO_2$, and $Sn_3(PO_4)_4$ may be used.

The method of preparing the catalyst system according to the present disclosure, in which the catalytically active metal containing the transition metal and tin (Sn) is supported on the basic support, includes a) preparing a support solution by dispersing a support in water or an organic solvent, b) adding precursors of a transition metal and tin as active components to the support solution and then performing stirring, c) drying the resulting catalyst precursor solution to obtain a dried product, d) firing the dried product to obtain a fired product, and e) reducing the fired product to obtain a catalyst system on which the catalytically active metal is supported.

Here, step a) may be replaced with a') preparing a solution in which precursors of a transition metal and tin, as active components, are dissolved, and step b) may be replaced with b') dispersing a support in the solution in which the transition metal precursor and the tin precursor are dissolved. Steps a) and b) may be performed simultaneously, so the support and the active component metal precursors may be added simultaneously.

The precursors of step b) or b') may be directly added to the solution of step a) or a'), or the precursors of step b) or b') may be dissolved in individual solvents, and the dissolved solutions may then be added to the solution of step a) or a').

The firing of step d) may be omitted, and step e) may be performed immediately.

In addition, a method of preparing a catalyst according to the present disclosure includes i) preparing a solution in which a precursor of a material used as a support and precursors of a transition metal and tin as active metal components are weighed and dissolved in a solvent, ii) adjusting the pH of the solution, iii) aging the solution after step ii) at a predetermined temperature, iv) subjecting a precipitate in the solution after step iii) to filtering, selective washing, and drying, v) firing the dried precipitate, and vi) reducing the fired product.

In step i), the precursor of the material used as the support and the precursors of metals used as the active metal components may be simultaneously added to the solvent to prepare a solution, or solutions obtained by individually dissolving the precursors may be mixed together. Here, the mixing sequence is that the active metal precursors may be mixed first and then mixed with the precursor of the material used as the support, or conversely, the solution of the precursor of the material used as the support may be mixed with the active metal precursors. The support precursor and the transition metal precursor may be mixed first, and then the tin precursor may be added thereto, or the support precursor and the tin precursor may be mixed first, and then the transition metal precursor may be added thereto, and there may be variations in the mixing sequence. However, when step i) is not a single step but is sequential mixing, adjusting the pH in step ii) may be performed after sequential mixing, and the aging of step iii) may be performed after final mixing, or may be performed after mixing in each step.

Therefore, in the preparation sequence of the catalyst, steps i), ii) and iii) may be repeated as needed, and thus may progress in the sequence of i)→ii)→iii)→i)→ii)→iii) . . . vi)→v)→vi), or in the sequence of i)→ii)→i)→ii) . . . iii)→vi)→v)→vi). Here, the firing of step v) may be omitted, and the reducing of step vi) may be performed immediately.

The aging may be performed in a manner in which the solution is allowed to stand in the state in which heat is applied thereto, or is allowed to stand without separate heating.

For the adjustment of the pH, a basic material or an acidic material may be used, and NaOH is preferably used.

Moreover, the reduction step is performed through reduction in a liquid phase using a reducing agent such as hydrazine, $NaBH_4$, etc. or through heat treatment in a hydrogen atmosphere, which controls the dispersion degree and specific surface area of the active metal, removes impurities from the catalyst, and increases bonding strength between the active metal and the support. This step is preferably conducted in the temperature range of room temperature to 500° C.

In the reduction step, all of the metals present in the catalytically active metal may be reduced, or only some thereof may be reduced. For example, when Ru and Sn are used as active metal components, Ru may be in the form of being reduced to a metal, but Sn may be present in a form such as $Sn^{2+}$, $Sn^{4+}$, etc. in which a portion of Sn is not reduced to a metal but is bound with oxygen, etc. Also, the transition metal and Sn contained in the catalytically active metal may be provided in the form of an alloy.

Figure 2:
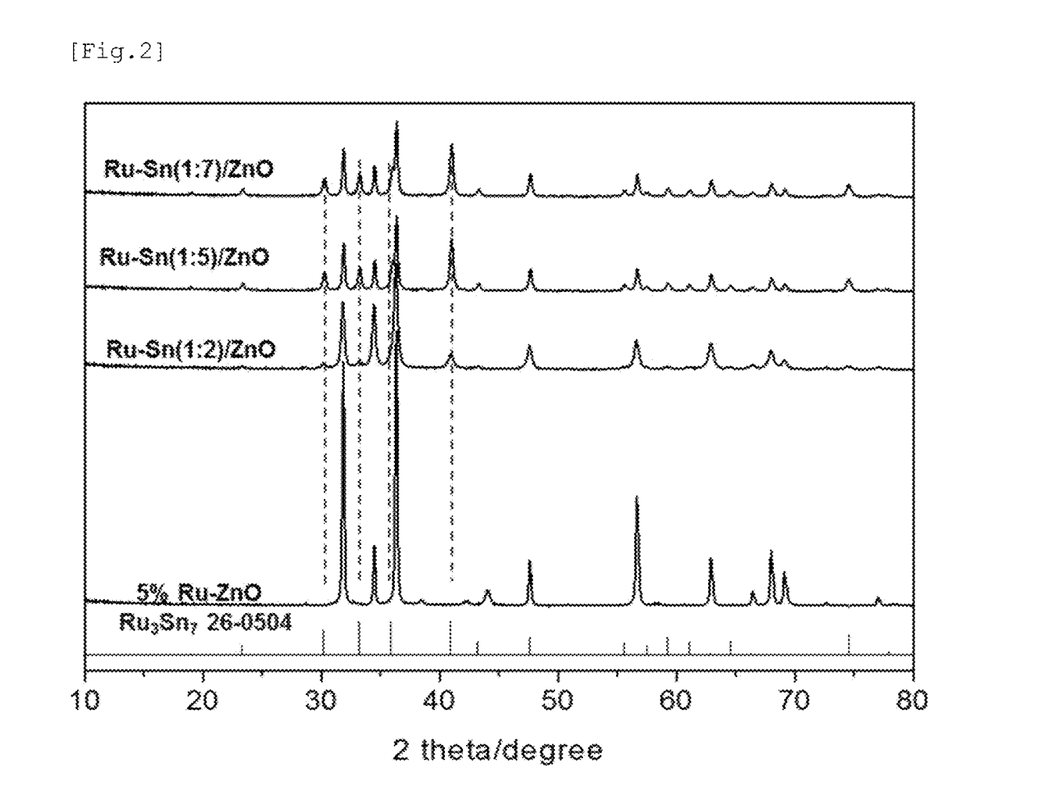
FIG. 2 shows XRD data after reduction of catalyst systems in which Ru or Ru and Sn are supported on ZnO.

The results of measurement of XRD to confirm the state after reduction of the catalytically active metal are shown in FIG. 2. With reference to FIG. 2, it can be seen that, when only Ru is supported on ZnO, the alloy phase of Ru and Sn does not appear, but when both Ru and Sn are supported simultaneously, the metal alloy phase such as $Ru_3Sn_7$ is present.

In addition, a method of preparing 1,2-pentanediol according to the present disclosure includes reacting a starting material including at least one of furfural and furfuryl alcohol with hydrogen in the presence of the catalyst, in which the active metal including at least one transition metal and tin (Sn) is supported on the basic support.

The furfural and/or furfuryl alcohol may be compounds derived from biomass, and specifically may be derived from hemicellulose. The material that occupies most of the hemicellulose is xylan, and furfural may be easily obtained by decomposing xylan into xylose, which is pentose, through hydrolysis, and dehydrating xylose.

The catalyst may be used in an amount of 0.001 to 25 wt % based on the amount of the starting material, and if the amount of the catalyst is less than 0.001 wt %, sufficient catalytic activity may not appear, whereas if the amount of the catalyst exceeds 25 wt %, economic benefits may be negated in view of the effect of increasing the catalytic activity depending on the amount of the catalyst.

When a starting material such as furfural and/or furfuryl alcohol is reacted with hydrogen using the catalyst of the present disclosure, in which the active metal including at least one transition metal and tin (Sn) is supported on the basic support, the reaction yield of 1,2-pentanediol increases.

The reaction yield of 1,2-pentanediol is preferably 40% or more, more preferably 70% or more, and most preferably 80% or more.

The reaction in the presence of the catalyst may proceed in a liquid phase or a gas phase.

When the reaction in the presence of the catalyst proceeds in a liquid phase, the reaction is preferably carried out under conditions of a reaction temperature of 100 to 200° C. and a hydrogen pressure of 5 to 50 bar. If the hydrogen pressure is less than 5 bar, the reaction rate may be slow, whereas if the hydrogen pressure exceeds 50 bar, the reaction yield of byproducts may increase and thus the reaction yield of 1,2-pentanediol may decrease, which is undesirable.

When the reaction of the present disclosure proceeds in a liquid phase, the starting material is reacted in a state in which the liquid phase is maintained, and the starting material may be used by being diluted in a solvent capable of dissolving the starting material. Here, the solvent is preferably used in an amount of 25 to 1000 wt %, and more preferably 100 to 500 wt %, based on the amount of the starting material. Unlimited examples of the solvent may include alcohol, GBL (gamma-butyrolactone), water, and mixtures thereof. Preferably, the solvent is an alcohol, and is more preferably 1-propanol, isopropanol, 1-butanol, 2-butanol, or mixtures thereof.

Since the alcohol solvent has high solubility of furfural and furfuryl alcohol and does not contain a highly reactive site, it does not cause changes in functional groups or in rapid chemical properties in the reaction with hydrogen, and thus constant reaction conditions may be provided during the reaction process.

When the reaction in the presence of the catalyst proceeds in a gas phase, the reaction is preferably carried out under conditions of a reaction temperature of 200 to 300° C. and a hydrogen pressure of 5 to 100 bar. If the hydrogen pressure is less than 5 bar, the reaction rate may be slow, whereas if the hydrogen pressure exceeds 100 bar, the reaction yield of byproducts may increase and thus the reaction yield of 1,2-pentanediol may decrease, which is undesirable.

The reaction in the presence of the catalyst may take place in a reactor through which a gas stream continuously flows. The gas stream in the reactor includes the starting material (including furfural and/or furfuryl alcohol), hydrogen, and optionally, an inert gas, and the gas hourly space velocity (GHSV) of the gas stream relative to the volume of the catalyst is 500 to 50,000 h$^{-1}$, and preferably 500 to 900 h$^{-1}$. If the gas hourly space velocity of the gas stream is less than 500 h$^{-1}$, the reaction proceeds well, but the amount of the product is too small, which is undesirable in view of industrial applicability.

The reactor in the presence of a heterogeneous catalyst in a gas phase is a tubular reactor packed with a heterogeneous catalyst.

A feed stream injected into the tubular reactor via suitable metering devices is composed of a starting material including at least one selected from the group consisting of furfuryl alcohol and furfural, the required amount of hydrogen, and, optionally, an inert gas. The starting material may be converted into a gas phase using a saturator for heating liquid furfuryl alcohol and/or furfural to a temperature of 80 to 120° C., preferably 90 to 110° C., and flows of hydrogen or hydrogen and an inert gas may be used by passing through the liquid starting material, or the liquid starting material may be placed in an evaporator using a metering pump or the like and thus vaporized and used.

A better understanding of the catalyst for preparing 1,2-pentanediol according to the present disclosure and the reaction for preparing 1,2-pentanediol using the same may be obtained through the following preparation examples and experimental examples.

In the following description of preferred embodiments of the present disclosure, detailed descriptions of known functions and components incorporated herein will be omitted when the same may make the subject matter of the present disclosure unclear.

MODE FOR DISCLOSURE

<Preparation Example> Method of Preparing Catalyst

Preparation Example 1: Preparation of 5 wt % Ru/ZnO 5 wt % Ru/ZnO was prepared through precipitation and deposition as follows.

$Zn(NO_3)_2 \cdot 6H_2O$ was used as a Zn precursor, and $RuCl_3 \cdot xH_2O$ was used as a Ru precursor. $Zn(NO_3)_2 \cdot 6H_2O$ and $RuCl_3 \cdot xH_2O$ were weighed such that the mass converted to Ru became 5 wt % of the mass converted to ZnO, and an aqueous solution in which these precursors were dissolved in distilled water was stirred for 5 hours while the pH thereof was maintained at 7.2-7.5 through dropwise addition of a 2.0 M NaOH solution at room temperature, and was then allowed to stand at 85° C. for 5 hours.

Thereafter, a precipitate in the solution was filtered and then fired at 450° C. for 6 hours in an ambient atmosphere. The fired catalyst was reduced at 420° C. for 2 hours in a 5% $H_2/N_2$ atmosphere before use for the reaction.

Preparation Examples 2 to 4: Preparation of 4.1 wt % Ru—Sn/ZnO

The alloy catalyst of Ru and Sn was prepared through coprecipitation and deposition as follows.

$Zn(NO_3)_2 \cdot 6H_2O$, $SnCl_4 \cdot 5H_2O$ and $RuCl_3 \cdot xH_2O$ were weighed such that the total mass of Ru and Sn metals was 4.1 wt % relative to the mass of ZnO. Here, the molar ratio of Ru and Sn was adjusted to 1:2 (Preparation Example 2), 1:5 (Preparation Example 3) or 1:7 (Preparation Example 4).

The weighed $Zn(NO_3)_2 \cdot 6H_2O$ was dissolved in water to obtain a 0.1 M aqueous solution, and the $SnCl_4 \cdot 5H_2O$ was dissolved in water to obtain a 1 M aqueous solution, after which these aqueous solutions were added dropwise to 200 ml of distilled water at room temperature and then stirred for 12 hours while the pH of the solution was maintained at 7.5 using 2 M NaOH.

To the solution thus obtained, a 0.5 M RuCl$_3$.xH$_2$O aqueous solution was added dropwise, followed by stirring for 1 hour while maintaining the pH of the solution at 7.2 using 2 M NaOH. After completion of addition of the 0.5 M RuCl$_3$.xH$_2$O aqueous solution, the resulting solution was stirred at room temperature for 5 hours and then allowed to stand at 85° C. for 5 hours.

Next, the resulting precipitate was filtered, washed with water to remove Na and Cl ions, and then dried at 120° C. for 12 hours, and the dried product was reduced at 420° C. for 2 hours in a 5% H$_2$/N$_2$ atmosphere before use for the reaction.

Preparation Example 5: Preparation of 5 wt % Pt/Hydrotalcite 0.95 g of hydrotalcite was placed in a solution in which 0.1050 g of H$_2$PtCl$_6$.xH$_2$O was dissolved in 100.0 ml of distilled water, and excess water was evaporated at 60° C. using a rotary evaporator, followed by firing at 450° C. for 6 hours in an ambient atmosphere to obtain a 5 wt % Pt/hydrotalcite catalyst. The catalyst was reduced at 420° C. for 2 hours in a 5% H$_2$/N$_2$ atmosphere before use for the reaction.

Preparation Example 6: Preparation of 4.1 wt % 1Ru-5Sn/Hydrotalcite

Mg—Al hydrotalcite (Mg/Al=3) was prepared through coprecipitation. 19.23 g of Mg(NO$_3$)$_2$.6H$_2$O and 7.67 g of Al(NO$_3$)$_2$ 9H$_2$O were added to 200 ml of deionized water, and to the resulting solution, 100 ml of a 0.5 M Na$_2$CO$_3$ aqueous solution was slowly added so that precipitation proceeded. The pH of the solution was adjusted to 10 using 2.0 M NaOH. The resulting precipitate was allowed to stand at 100° C. for 24 hours and then washed with deionized water until the filtered solution became neutral. The filtered solid was dried at 120° C. for 12 hours and then fired at 450° C. for 10 hours using steam. The fired sample was again added to 200 ml of deionized water, followed by sonication while allowing nitrogen to flow at 50° C. for 24 hours. The solid was filtered and then dried at 80° C. for 12 hours to obtain Mg—Al hydrotalcite.

The Mg—Al hydrotalcite thus obtained was placed in an aqueous solution of SnCl$_4$.5H$_2$O and RuCl$_3$.xH$_2$O weighed such that the total mass converted to Ru and Sn was 4.1 wt %, after which Ru and Sn were supported through coprecipitation. Here, the molar ratio of Ru and Sn was adjusted to 1:5. Excess water was evaporated at 60° C. using a rotary evaporator. The catalyst was dried for 12 hours in an ambient atmosphere and then reduced at 420° C. for 2 hours in a 5% H$_2$/N$_2$ atmosphere.

Preparation Example 7: Preparation of 4.1 wt % 1Pt-5Sn/ZnO

Supporting was performed in the same manner as in Preparation Example 2, with the exception that Pt was used in lieu of Ru. Here, the Pt precursor that was used was H$_2$PtCl$_6$.xH$_2$O.

Preparation Example 8: Preparation of 6.1 wt % 1Ni-1Sn/ZnO

The alloy catalyst of Ni and Sn was prepared through coprecipitation as follows.

Zn(NO$_3$)$_2$.6H$_2$O, SnCl$_4$.5H$_2$O and Ni(NO$_3$)$_2$.6H$_2$O were weighed such that the total mass of Ni and Sn metals was 6.1 wt % relative to the mass of ZnO. Here, the molar ratio of Ni and Sn was adjusted to 1:1.

Specifically, 34.99 g of Zn(NO$_3$)$_2$.6H$_2$O and 0.99 g of SnCl$_4$.5H$_2$O were dissolved in 400 mL of distilled water and 200 mL of distilled water, respectively, and then these two solutions were mixed together. The resulting solution was mixed with 200 mL of a 0.02 M Ni(NO$_3$)$_2$.6H$_2$O aqueous solution and then stirred for 12 hours while the pH of the solution was maintained at 9.0 using 2 M NaOH.

After further stirring at 80° C. for 5 hours, the resulting precipitate was filtered, washed with water to remove Na and Cl ions, dried at 120° C. for 12 hours, and fired at 550° C. for 6 hours, and the dried product was reduced at 500° C. for 4 hours in a 5% H$_2$/N$_2$ atmosphere before use for the reaction.

Preparation Examples 9-10: Preparation of 4.1 wt % 1Ru-5Sn/SiO$_2$, 4.1 wt % 1Ru-5Sn/Al$_2$O$_3$ A 4.1 wt % 1Ru-5Sn/support was prepared by mixing Ru and Sn precursors in the same manner as above, with the exception of using SiO$_2$ (Preparation Example 9) and Al$_2$O$_3$ (Preparation Example 10) as the support using a wet impregnation process. Here, hydrotalcite, SnCl$_4$.5H$_2$O and RuCl$_3$.xH$_2$O were weighed such that the total mass of Ru and Sn metals was 4.1 wt % relative to the mass of the support SiO$_2$ or Al$_2$O$_3$. The molar ratio of Ru and Sn was adjusted to 1:5. The catalyst was reduced at 420° C. for 2 hours in a 5% H$_2$/N$_2$ atmosphere before use for the reaction.

Preparation Example 11: Preparation of 5 wt % Ru/(8:2)SnO$_2$—SiO$_2$

First, 13.75 g of a Ludox-SM30 (400 ml) aqueous solution and 37.0 g of SnCl$_4$.5H$_2$O (400 ml) were mixed and then slowly mixed (dropwise) while the pH thereof was maintained at 8.5 using 2 M NaOH. The mixed solution was stirred at room temperature for 5 hours and then allowed to stand at 85° C. for 5 hours, after which the resulting precipitate was filtered, washed with distilled water, dried, and then fired in air at 450° C. to obtain (8:2)SnO$_2$—SiO$_2$ at a mass ratio of SnO$_2$ and SiO$_2$ of 8:2.

The (8:2)SnO$_2$—SiO$_2$ thus obtained was placed in an aqueous solution of RuCl$_3$.xH$_2$O weighed such that the mass converted to Ru was 5 wt %, and Ru was supported through impregnation. Excess water was evaporated at 60° C. using a rotary evaporator.

The 5 wt % Ru/(8:2)SnO$_2$—SiO$_2$ thus obtained was fired at 450° C. for 6 hours in an ambient atmosphere, and the fired catalyst was reduced at 420° C. for 2 hours in a 5% H$_2$/N$_2$ atmosphere before use for the reaction.

Preparation Example 12: Preparation of 5 wt % Cu/(8:2)SnO$_2$—SiO$_2$ 5 wt % Cu/(8:2) SnO$_2$—SiO$_2$ was prepared in the same manner as in Preparation Example 11, with the exception that Cu(NO$_3$)$_2$.6H$_2$O, weighed such that the mass of Cu metal was 5 wt % relative to the mass of (8:2) SnO$_2$—SiO$_2$, was used in lieu of RuCl$_3$.xH$_2$O.

Preparation Example 13: Preparation of 4.1 wt % 1(Cu—Ni)-5Sn/SiO$_2$

Cu(NO$_3$)$_2$.6H$_2$O, Ni(NO$_2$)$_2$.6H$_2$O, and SnCl$_4$.5H$_2$O were weighed such that the total mass of Cu, Ni and Sn metals was 4.1 wt % relative to the mass of $SiO_2$. Then, the same procedures were performed as in Preparation Example 9, with the exception that the molar ratio of (Cu+Ni) and Sn was set to 1:5 and the molar ratio of Cu and Ni was adjusted to 1:1, thereby obtaining 4.1 wt % 1 (Cu—Ni)-5Sn/$SiO_2$.

<Experimental Example 1> Experiment for Preparation of 1,2-Pentanediol by Liquid Phase Reaction Using the catalysts prepared in Preparation Examples above, an experiment for the preparation of 1,2-pentanediol was carried out as follows.

Into a 100 ml stainless steel autoclave reactor equipped with a Teflon container, 0.1 g of the catalyst prepared in each of Preparation Examples above, 10 ml of anhydrous isopropanol and 1 ml of furfural were added and purged with hydrogen three times or more to replace the atmosphere in the container with hydrogen. After applying the pressure with high-pressure hydrogen and raising the temperature to the reaction temperature, the reaction was carried out for a predetermined time. Here, stirring was performed using a Teflon magnetic bar at a stirring speed of 1000 rpm. The hydrogen pressure, the reaction temperature, and the reaction time are shown in Table 1 below.

After the reaction, the temperature was lowered to room temperature, the catalyst was removed through simple filtration, and the solution in the reactor was collected and analyzed by GC (FID) using a CycloSil-B column (30 m×0.32 mm×0.25 μm). The results thereof are shown in Table 1 below.

Table 1 below shows the results of calculation of the reaction yield of 1,2-pentanediol synthesized through reaction with hydrogen using the catalyst prepared in Preparation Example.

In Table 1 below, furfural conversion % and C Yield were calculated as follows.

$$\text{Furfural } Conv. \% = \frac{\text{Furfural}_{(unreacted)(mol)}}{\text{Furfural}_{(initial)(mol)}} \times 100 \quad \text{(Equation 1)}$$

$$\text{Product Yield } (C \%) = \frac{\text{Product}_{(mol)} \times \text{Product}_{(C\ atom)}}{\text{Reactant}_{(mol)} \times \text{Reactant}_{(C\ atom)}} \times 100 \quad \text{(Equation 2)}$$

TABLE 1

| Preparation Example | Catalyst | Temperature (°C.) | Time (h) | Pressure (bar) | Furfural Conv. % | Furfuryl alcohol | MTHF | 1,2-PDO | 1,5-PDO | Others |
|---|---|---|---|---|---|---|---|---|---|---|
| 1 | 5 wt % Ru/ZnO | 150 | 4 | 30 | 100 | 60.9 | 27 | — | — | 12.1 |
|   |   |   | 6 |   | 100 | 49.6 | 36 | — | — | 14.4 |
| 2 | 4.1 wt % 1Ru—2Sn/ZnO | 150 | 4 | 30 | 100 | 9.4 | 7.1 | 43.6 | 28.3 | 11.6 |
|   |   |   | 6 |   | 100 | 5.2 | 6.3 | 42.2 | 29.6 | 16.7 |
| 3 | 4.1 wt % 1Ru—5Sn/ZnO | 150 | 5 | 30 | 100 | 0 | 0.4 | 84.2 | 9.1 | 6.3 |
|   |   |   | 6 | 25 | 100 | 0 | 0 | 86.3 | 11.2 | 2.3 |
|   |   | 140 | 5 | 35 | 100 | 0 | 0 | 87.3 | 12.1 | 0.6 |
|   |   | 130 | 5 | 35 | 100 | 6.9 | 0 | 78.2 | 11.3 | 3.6 |
|   |   |   | 6 |   | 100 | 0 | 0 | 83.6 | 12.4 | 4.0 |
|   |   | 100 | 6 | 35 | 100 | 81.4 | 0 | 9.3 | 5.8 | 3.5 |
|   |   |   | 6 | 25 | 100 | 88.2 | 0 | 5.9 | 2.6 | 3.3 |
|   |   |   | 6 | 15 | 100 | 96.2 | 0 | 1.1 | 0.3 | 2.4 |
|   |   |   | 6 | 5 | 81 | 76 | 0 | 0 | 0 | 5.0 |
| 4 | 4.1 wt % 1Ru—7Sn/ZnO | 150 | 6 | 30 | 100 | 0 | 0 | 81.3 | 14.2 | 4.5 |
|   |   | 140 | 6 | 30 | 100 | 0 | 0 | 84.9 | 11.3 | 3.8 |
| 5 | 5 wt % Pt/HT | 140 | 6 | 30 | 100 | 15.3 | 0 | 54.4 | 18.2 | 12.1 |
| 6 | 4.1 wt % 1Ru—5Sn/HT (Mg/Al = 3) | 140 | 6 | 30 | 100 | 32.1 | 0 | 41.9 | 12.2 | 13.8 |
| 7 | 4.1 wt % 1Pt—5Sn/ZnO | 140 | 6 | 30 | 100 | 3.1 | 0 | 79.1 | 13.6 | 4.2 |
| 8 | 6.1 wt % 1Ni—1Sn/ZnO | 140 | 6 | 30 | 100 | 20.2 | 0 | 64.6 | 10.4 | 4.8 |
|   |   | 160 | 6 | 30 | 100 | 3.1 | 0 | 80.1 | 15.1 | 1.7 |
| 9 | 4.1 wt % 1Ru—5Sn/$SiO_2$ | 140 | 6 | 30 | 100 | 75.2 | 0 | 8.3 | 12.9 | 3.6 |
| 10 | 4.1 wt % 1Ru—5Sn/$Al_2O_3$ | 140 | 6 | 30 | 100 | 80.2 | 0 | 7.6 | 8.8 | 3.4 |
| 11 | 5 wt % Ru/(8:2)$SnO_2$—$SiO_2$ | 140 | 6 | 30 | 100 | 9.3 | 25.6 | 32.3 | 20.1 | 12.7 |
| 12 | 5 wt % Cu/(8:2) $SnO_2$—$SiO_2$ | 140 | 6 | 30 | 100 | 83 | 0 | 6.4 | 1.7 | 8.9 |
| 13 | 4.1 wt % 1 (Cu—Ni)—5Sn/$SiO_2$ | 140 | 6 | 30 | 100 | 79.3 | 0 | 6.7 | 10.1 | 3.9 |

1,2-PDO: 1,2-pentanediol,
1,5-PDO: 1,5-pentanediol,
MTHF: methyltetrahydrofuran,
HT: hydrotalcite As is apparent from Table 1, when using the catalyst in which 5 wt % of ruthenium was supported alone as a transition metal (Preparation Example 1), the reaction of 1,2-pentanediol did not occur, but when using the catalyst in which both ruthenium and tin were supported in a total weight of 4.1 wt % (Preparation Examples 2 to 4), the production of 1,2-pentanediol was confirmed even though the amount of the active metal that was supported was decreased. The reactivity also differs depending on the relative molar ratio of ruthenium and tin. When the molar ratio of tin/ruthenium was increased from 2 to 5, the reaction yield of 1,2-pentanediol was greatly increased from 42.2% to 84.2% despite the short reaction time under the same conditions.

In addition, even with the same active metal, when using the basic support such as ZnO or hydrotalcite, the yield of 1,2-pentanediol was much higher than when using the support such as silica or alumina, indicating that not only the type of active metal but also the properties of the support are regarded as very important in the present catalyst system.

Preparation Example 14: Preparation of 10 wt % 1Ni-1Sn/ZnO

The alloy catalyst of Ni and Sn was prepared through coprecipitation as follows.

$Zn(NO_3)_2.6H_2O$, $SnCl_4.5H_2O$ and $Ni(NO_3)_2.6H_2O$ were weighed such that the total mass of Ni and Sn metals was 10 wt % relative to the mass of ZnO. Here, the molar ratio of Ni and Sn was adjusted to 1:1.

Specifically, all of a solution of 32.9 g of $Zn(NO_3)_2.6H_2O$ in 400 ml of distilled water, a solution of 1.64 g of $Ni(NO_3)_2.6H_2O$ in 400 ml of distilled water, and 1.98 g of $SnCl_4.5H_2O$ in 400 ml of distilled water were slowly added dropwise to 200 ml of distilled water and mixed together. Here, the pH of the solution was maintained at 8.5-9 through dropwise addition of 2 M NaOH. After formation of the precipitate, the solution was stirred at room temperature for 12 hours.

Thereafter, the solution was further stirred at room temperature for 5 hours and allowed to stand at 85° C. for 5 hours, after which the resulting precipitate was filtered, washed with water to remove Na and Cl ions, dried at 120° C. for 12 hours in an ambient atmosphere, and compressed and pulverized. The particles having a size of 320 to 420 μm were sieved, the particles thus obtained were fired at 550° C. for 6 hours in an ambient atmosphere, and the fired product was reduced at 500° C. for 4 hours in a 5% $H_2/N_2$ (50 cc/min) atmosphere before use for the reaction.

Preparation Example 15: Preparation of 10 wt % 1Cu-1Sn/ZnO 10 wt % 1Cu-1Sn/ZnO was prepared in the same manner as in Preparative Example 14, with the exception that $Cu(NO_3)_2.6H_2O$ (32.9 g in 400 ml of $H_2O$) was used in lieu of $Ni(NO_3)_2.6H_2O$ (1.64 g in 400 ml of $H_2O$), $SnCl_4.5H_2O$ (1.893 g in 400 ml of $H_2O$) was used in lieu of $SnCl_4.5H_2O$ (1.98 g in 400 ml of $H_2O$), and final reduction was performed at 300° C.

Preparation Example 16: Preparation of 10 wt % 1Co-1Sn/ZnO 10 wt % 1Co-1Sn/ZnO was prepared in the same manner as in Preparative Example 14, with the exception that $Co(NO_3)_2.6H_2O$ (32.9 g in 400 ml of $H_2O$) was used in lieu of $Ni(NO_3)_2.6H_2O$ (1.64 g in 400 ml of $H_2O$), $SnCl_4.5H_2O$ (1.978 g in 400 ml of $H_2O$) was used in lieu of $SnCl_4.5H_2O$ (1.98 g in 400 ml of $H_2O$), and final reduction was performed at 400° C.

Preparation Example 17: Preparation of 4.1 wt % 1Ru-7Sn/ZnO $Zn(NO_3)_2.6H_2O$, $SnCl_4.5H_2O$ and $RuCl_3.xH_2O$ were weighed such that the total mass of Ru and Sn metals was 4.1 wt % relative to the mass of ZnO. Here, the molar ratio of Ru and Sn was adjusted to 1:7.

The weighed $Zn(NO_3)_2.6H_2O$ was dissolved in water to obtain a 0.1 M aqueous solution, the $SnCl_4.5H_2O$ was dissolved in water to obtain a 1 M aqueous solution, these aqueous solutions were then added dropwise to 200 ml of distilled water at room temperature, and the pH of the solution was maintained at 7.5 using 2 M NaOH. After precipitation and then stirring for 12 hours, a 0.5 M $RuCl_3.xH_2O$ aqueous solution was added dropwise to the solution stirred above, and the pH of the solution was maintained at 7.2 using 2 M NaOH. After completion of addition of the 0.5 M $RuCl_3.xH_2O$ aqueous solution, the resulting solution was stirred at room temperature for 5 hours and then allowed to stand at 85° C. for 5 hours.

Next, the resulting precipitate was filtered, washed with water to remove Na and Cl ions, dried at 120° C. for 12 hours in an ambient atmosphere, and compressed and pulverized, and the particles having a size of 320 to 420 μm were sieved. The dried product thus obtained was reduced through direct reduction without firing.

Preparation Example 18: Preparation of 10 wt % Ni/ZnO 10 wt % Ni/ZnO was prepared in the same manner as in Preparative Example 14, with the exception that a Ni precursor was used alone, without the use of the Sn precursor, and $Ni(NO_3)_2.6H_2O$, weighed such that the mass of Ni metal was 10 wt % relative to the mass of ZnO, was supported.

Preparation Example 19: Preparation of 10 wt % 1Ni-1Sn/γ-$Al_2O_3$ 10 wt % 1Ni-1Sn/γ-$Al_2O_3$ was prepared in the same manner as in Preparative Example 14, with the exception that γ-$Al_2O_3$ (9.0 g) was used as the support.

Preparation Example 20: Preparation of 10 wt % 1Ni-1Sn/$CeO_2$ 10 wt % 1Ni-1Sn/$CeO_2$ was prepared in the same manner as in Preparative Example 14, with the exception that an aqueous solution (22.7 g/400 mL) of $Ce(NO_3)_3*6H_2O$ as a support precursor was slowly added dropwise to 200 mL of an aqueous solution along with Ni and Sn and mixed together.

<Experimental Example 2>: Experiment for Preparation of 1,2-Pentanediol by Gas Phase Reaction Using the catalysts prepared in Preparation Examples above, an experiment for the preparation of 1,2-pentanediol by reacting furfuryl alcohol with hydrogen in a gas phase was carried out as follows.

The measurement of the activity of the catalyst was performed in a fixed-bed downstream stainless steel (SUS 316) reactor under pressure. The preheating zone was kept at 250° C. to evaporate furfuryl alcohol. The catalyst (1.0 g) was located in the middle portion of the reactor using quartz wool as a support. The reaction was carried out at 220-280° C., and the hydrogen pressure was monitored using a pressure regulator connected to the reactor and a hydrogen gas line. Furfuryl alcohol was mixed at 10 wt % in isopropyl alcohol and introduced into the reactor at a WHSV of 1.0 using a liquid metering pump along with hydrogen (at a flow rate of 61 cc/min).

The gas components of the reaction mixture ($H_2$ and gaseous hydrocarbon) were analyzed by TCD using on-line gas chromatography (Donam Instruments DS6200) equipped with a carbon sphere capillary tube. 1,2-pentanediol (1,2-PDO), 1,5-pentanediol (1,5-PDO), methyltetrahydrofuran, tetrahydrofurfuryl alcohol (THFA), 2-methylfuran (2MF), 2-methyltetrahydrofuran (MTHF), 1-pentanol (PO), 1,4-pentanediol (1,4-PDO), tetrahydrofuran (THF), etc. were collected every 10 hours and detected using a flame ionization detector (FID), CycloSil-B column (0.32 mm×30), and HP-5. The carbon mass balance of the liquid product was estimated to be 97% or more. The catalyst performance was evaluated based on the furfuryl alcohol conversion and the yield of 1,2-PDO.

The results of catalytic activity are shown in Table 2 below.

In Table 2 below, furfuryl alcohol conversion was calculated by substituting the number of moles of furfuryl alcohol in lieu of furfural into Equation 1, and C Yield was calculated as in Equation 2.

(Preparation Example 19) as an acidic support were compared. When the $CeO_2$ support was used, 1,2-PDO selectivity was slightly decreased compared to when ZnO was used, whereas when $\gamma$-$Al_2O_3$ was used, selectivity was significantly decreased, indicating that the basic support is an important factor.

Although the preferred embodiments of the present disclosure have been disclosed for illustrative purposes with reference to the accompanying drawings, those skilled in the art will appreciate that various modifications and equivalents are possible, without departing from the scope and spirit of the disclosure as disclosed in the accompanying claims. Therefore, the scope of the present disclosure should be determined based on the accompanying claims.

The invention claimed is:

1. A method of preparing 1,2-pentanediol through a hydrogenation reaction of a starting material comprising at least one of furfural and furfuryl alcohol in presence of a catalyst,
   wherein
   the catalyst is that a catalytically active metal is supported on a basic support,

TABLE 2

| Preparation Example | Catalyst | Temp. (° C.) | $H_2$ Press. (bar) | Furfuryl alcohol Conv. % | C Yield (%) | | | | |
|---|---|---|---|---|---|---|---|---|---|
| | | | | | MTHF | 1,2-PDO | 1,5-PDO | THFA | 2MF | Others |
| 14 | 10 wt % 1Ni—1Sn/ZnO | 230 | 30 | 100 | 0 | 84.1 | 11.8 | 3.2 | 0.6 | 0.3 |
| | | 230 | 40 | 100 | 0 | 90.4 | 9.1 | 0.3 | 0.2 | 0 |
| | | 250 | 40 | 100 | 0 | 91.4 | 8.4 | 0.2 | 0 | 0 |
| 15 | 10 wt % 1Cu—1Sn/ZnO | 250 | 40 | 100 | 0 | 70.8 | 23.2 | 4.3 | 1.4 | 0.3 |
| 16 | 10 wt % 1Co—1Sn/ZnO | 250 | 40 | 100 | 0 | 73.2 | 21.6 | 3.2 | 1.5 | 0.5 |
| 17 | 4.1 wt % 1Ru—7Sn/ZnO | 250 | 40 | 100 | 0 | 77.4 | 17.7 | 2.8 | 1.2 | 0.9 |
| 18 | 10 wt % Ni/ZnO | 250 | 40 | 100 | 47.2 | 17.3 | 28.4 | 5.1 | 1.2 | 0.8 |
| 19 | 10 wt % 1Ni—1Sn/$\gamma$-$Al_2O_3$ | 250 | 40 | 100 | 3.2 | 38 | 37.7 | 14.9 | 5.1 | 1.1 |
| 20 | 10 wt % 1Ni—1Sn/$CeO_2$ | 250 | 40 | 100 | 0 | 80.5 | 14.8 | 3.7 | 0.5 | 0.5 |

As is apparent from Table 2, all the catalysts that were used exhibited a furfuryl alcohol conversion of 100% under the experimental conditions, but the product distribution differed depending on experimental conditions such as temperature, pressure and the type of catalyst that was used.

In the experimental example using the catalyst of Preparation Example 14, the highest yield of 1,2-PDO was obtained when the reaction temperature was 250° C., and the yield of 1,2-PDO was also increased when the hydrogen pressure increased from 30 bar to 40 bar.

In addition, the yield of 1,2-PDO in the gas-phase catalytic reaction was the highest in the presence of the catalyst prepared in Preparation Example 14.

When comparing the reaction experiment results using the catalysts of Preparation Example 18 and Preparation Example 14, the yield of 1,5-PDO was higher before the addition of Sn, but the yield of 1,2-PDO was greatly increased in the presence of the catalyst of Preparation Example 14 to which Sn was added, indicating that the presence of Sn is essential for the conversion of furfuryl alcohol into 1,2-PDO.

In addition, in order to confirm the effect of the basic support, the activities of the catalysts using $CeO_2$ (Preparation Example 20) as another basic support and using $\gamma$-$Al_2O_3$ the catalytically active metal comprises tin and at least one metal other than copper among transition metals belonging to Groups 8, 9, 10, and 11, the catalytically active metal does not contain copper, and the basic support is at least one selected from the group consisting of MgO, CaO, BaO—ZnO, MgO—$Al_2O_3$, ZnO, $ZrO_2$, $CeO_2$, hydroxyapatite, $Mg_2Al_2O_4$, $ZnAl_2O_4$, $BaTiO_3$, $ZnTiO_3$, $Cs_2O$, CsX, wherein X=OH, Cl, Br, or I, Zr-based MOFs, Mg-based MOFs, Ca-based MOFs, Sr-based MOFs, Ba-based MOFs, $Mg_2Al_2O_4$, $ZnAl_2O_4$, $BaTiO_3$, and $ZnTiO_3$.

2. The method of claim 1, wherein the at least one of furfural and furfuryl alcohol, which is the starting material, is derived from biomass.

3. The method of claim 1, wherein the furfural is obtained through dehydration of xylose resulting from hydrolysis of xylan, and the furfuryl alcohol is obtained through hydrogenation of the furfural.

4. The method of claim 1, wherein the hydrogenation reaction is carried out at a temperature of 100 to 200° C. and a pressure of 5 to 50 bar, and the hydrogenation reaction proceeds in a liquid phase.

5. The method of claim 1, wherein the hydrogenation reaction is carried out at a temperature of 200 to 300° C. and a pressure of 5 to 100 bar, and the hydrogenation reaction proceeds in a gas phase.

6. The method of claim 1, wherein the starting material is reacted in a liquid phase by diluting the starting material in any one solvent selected from among 1-propanol, isopropanol, 1-butanol, 2-butanol, and mixtures thereof.

7. The method of claim 1, wherein the catalyst is used in an amount of 0.001 to 25 wt % based on an amount of the starting material.

* * * * *